(12) United States Patent
Doeberitz et al.

(10) Patent No.: US 7,306,926 B2
(45) Date of Patent: *Dec. 11, 2007

(54) METHOD FOR DETECTING CARCINOMAS IN A SOLUBILIZED CERVICAL BODY SAMPLE

(75) Inventors: Magnus Von Knebel Doeberitz, Ziegelhausen (DE); Rüdiger Ridder, Schriesheim (DE); Matthias Herkert, Heidelberg (DE); Anja Reichert, Nußloch (DE)

(73) Assignee: MTM Laboratories AG, Heidelberg (DE)

( * ) Notice: Subject to any disclaimer, the term of this patent is extended or adjusted under 35 U.S.C. 154(b) by 475 days.

This patent is subject to a terminal disclaimer.

(21) Appl. No.: 10/650,057

(22) Filed: Aug. 26, 2003

(65) Prior Publication Data

US 2004/0180388 A1 Sep. 16, 2004

Related U.S. Application Data

(63) Continuation-in-part of application No. 10/633,484, filed on Jul. 31, 2003.

(30) Foreign Application Priority Data

Aug. 1, 2002 (EP) .................................. 02017313

(51) Int. Cl.
*G01N 33/574* (2006.01)

(52) U.S. Cl. ...................... 435/7.23; 435/7.92; 436/64; 436/501; 530/350; 530/387.7; 530/389.7

(58) Field of Classification Search ............... 435/7.23, 435/7.92; 436/64, 501; 530/350, 387.7, 530/389.7

See application file for complete search history.

(56) References Cited

U.S. PATENT DOCUMENTS

| | | | |
|---|---|---|---|
| 4,281,061 A | | 7/1981 | Zuk et al. |
| 5,889,169 A | * | 3/1999 | Beach et al. ................ 536/23.5 |
| 6,033,847 A | | 3/2000 | Sherr et al. |
| 6,316,208 B1 | | 11/2001 | Roberts et al. |
| 6,403,383 B1 | * | 6/2002 | Casterlin et al. ............ 436/518 |
| 6,709,832 B1 | * | 3/2004 | Von Knebel Doeberitz et al. ......... 435/7.23 |
| 2001/0039023 A1 | | 11/2001 | Schubert |
| 2002/0086288 A1 | | 7/2002 | Bird et al. |
| 2003/0157482 A1 | | 8/2003 | Keesee et al. |

FOREIGN PATENT DOCUMENTS

| | | |
|---|---|---|
| EP | 0 723 156 | 12/1995 |
| EP | 1 217 377 | 12/2001 |
| WO | WO/9220796 A2 * | 11/1992 |
| WO | WO 99/04238 | 7/1998 |

OTHER PUBLICATIONS

Geradts et al. (Am. J. Pathol. Jun. 1999; 154 (6): 1665-1671).*
Ryder et al. (Clin. Chem. Dec. 1988 34 (12): 2513-2516).*
Khleif et al. (Proc. Natl. Acad. Sci. USA. Apr. 1996 93: 4350-4354).*
Sano et al. (Pathology International. 1998; 48: 580-585).*
Ikeda et al. (J. Histochem. Cytochem. 1998; 46 (3): 397-403).*
Wentzensen et al. Cancer. 2006; 107: 2307-13.*
Mao et al. Int. J. Cancer. 2007; 120: 2435-8.*
Suneja et al. Brain Res. Protocols. 1998; 3: 88-93.*
Castellano et al. Cancer Res. Nov. 1, 1997; 57: 4868-75.*
Plath et al. J. Cell Biol. Sep. 18, 2000; 150 (6): 1467-77.*
Gump et al. J. Biol. Chem. Feb. 28, 2003; 278 (9): 6619-22.*
Dai et al. Gastroenterology. 2000; 119: 929-42.*
Qualtiere et al. (J. Immunol. Nov. 1977; 119(5): 1645-1651).*
Dimitriadis et al. (Anal. Biochem. Oct. 1, 1979; 98 (2): 445-451).*
McCabe et al. (J. Immunol. Methods. Apr. 6, 1988; 108 (1-2): 129-135).*
Bhakdi (J. Biochem. Biophys. Methods. Jan.-Feb. 2, 1980; 2 (1): 79-90).*
Liggett et al. (J. Clin. Oncol. Mar. 1998;16 (3): 1197-1206).*
Geradts, et al., "Immunohistochemical Detection of the Cyclin-dependent Kinase Inhibitor 2/Multiple Tumor Suppressor Gene 1 (CDKN2/MTS1) Product p16$^{INK4A}$ in Archival Human Solid Tumors: Correlation with Retinoblastoma Protein Expression", *Cancer Research* 55: 6006-11 (1995).
Hirama, et al., "p16 (CDKN2/Cylin-dependent Kinase-+inhibitor/Multiple Tumor Suppressor-1) Gene Is Not Altered in Uterine Cervical Carcinomas or Cell Lines", *Modern Pathology*, 9(1) 26-31 (1996).

(Continued)

*Primary Examiner*—Stephen L. Rawlings
(74) *Attorney, Agent, or Firm*—Howrey LLP; Viola T. Kung

(57) ABSTRACT

The present invention relates to a method for the early diagnosis of carcinomas and their preliminary stages, which comprises determining the overexpression of a cell cycle regulatory protein in a solubilized body sample. The present invention is particularly directed to a method for detecting cervical carcinomas, cervical intraepithelial neoplasias, or cervical carcinomas in-situ from a solubilized cervical body sample of a human subject, by solubilizing the cervical body sample in a lysis buffer, and determining the overexpression of cyclin dependent kinase inhibitor p16 in the solubilized cervical sample. The invention also concerns a test kit usable for this purpose as well as an in-vitro diagnostic device.

14 Claims, 3 Drawing Sheets

OTHER PUBLICATIONS

Kelley, et al., "CDKN2 in HPV-Positive and HPV-Negative Cervical-Carcinoma Cell Lines", *Int. J. Cancer*, 63: 226-30 (1995).

Kim, et al., "Absence of $p15^{INK4B}$ and $p16^{INK4A}$ Gene Alterations in Primary Cervical Carcinoma Tissues and Cell Lines with Human Papillomavirus Infection", *Gynecologic Oncology*, 70: 75-9 (1998).

Kim, et al., "Underexpression of Cyclin-Dependent Kinase (CDK) Inhibitors in Cervical Carcinoma", *Gynecologic Oncology*, 71: 38-45 (1998).

Klaes, et al., "Overexpression of $p16^{INK4A}$ as a Specific Marker for Dysplastic and Neoplastic Epithelial Cells of the Cervix Uteri", *Int. J. Cancer*, 92: 276-284 (2001).

Milde-Langosch, et al., "P16/MTS1 and *p*RB expression in endometrial carcinomas", *Virchows Arch*, 434: 23-8 (1999).

Milde-Langosch, et al., *p16/MTS*1 Inactivation in Ovarian Carcinomas: High Frequency of rEduced.

Protein expression Associated with Hyper-Methylation or Mutation in Endometroid and Mucinous Tumors , *Int. J. Cancer*, 79: 61-5 (1998).

Nuovo, et al., "In situ detection of the hypermethylation-induced inactivation of the *p*16 gene as a early event in oncogenesis", *PNAS*, 96(22): 12754-9 (1999).

Sano, et al., "Expression Status of *p*16 Protein Is Associated with Human Papillomavirus Oncogenic Potential in Cervical and Genital Lesions", *American Journal of Pathology*, 153(6): 1741-8 (1998).

Sano, et al., "Immunohistochemical overexpression of *p*16 protein associated with intact retinoblastoma protein expression in cervical cancer and cervical intraepithelial neoplasia", *Pathology International*, 48: 580-5 (1998).

Serrano, et al., "A new regulatory motif in cell-cycle control causing specific inhibition of cyclin D/CDK4", *Nature*, 366: 704-7 (1993).

Shigemasa, et al., "*p*16 Overexpression: A Potential Early Indicator of Transformation in Ovarian Carcinoma", *J. Soc. Gynecol Invest.*, 4(2): 95-102 (1997).

Shim, et al., "Profiling of Differentially Expressed Genes in Human Primary Cervical Cancer by Complementary DNA Expression Array", *Clinical Cancer Research*, 4: 3045-50 (1998).

Tam, et al., "Differential Expression and Cell Cycle Regulation of the Cyclin-dependent Kinase 4 Inhibitor $p16^{INK4}$", *Cancer Research*, 54: 1816-20 (1994).

Wong, et al., "Methylation of $p16^{INK4A}$ in primary gynecologic malignancy", *Cancer Letters*, 136: 231-5 (1999).

Wong, et al., $p16^{INK4}$ and $p15^{INK4B}$ Alterations in Primary Gynecologic Malignancy, *Gynecologic Oncology* 65: 319-24 (1997).

He, et al., "Expression, Deletion And Mutation of p16 Gene in Human Gastric Cancer" *World J. of Gastroenterology* 7(4): 515-521 (2001).

Myung, et al., "Loss Of p16 And p27 Is Associated With Progression Of Human Gastric Cancer" *Cancer Letters* 153:129-136 (2000).

Nakao et al., "Induction of p16 During Immortalization HPV 16 and 18 and Not During Malignant Transformation" *British J of Cancer* 75(10):1410- 1416, 1997.

O'Nions, et al., "p73 Is Over-Expressed In Vulval Cancer Principally As The Δ2 Isoform" *British J. Cancer* 85(10):1551-1556 (Nov. 2001).

Sano, et al., "Overexpression Of p16 And P14ARF Is Associated With Human Papillomavirus Infection In Cervical Squamous Cell Carcinoma And Dysplasia" *Pathology Int.* 52:375-383 (May 2002).

Sherr, "The Ink4a/Arf Network in Tumor Suppression" *Nature Reviews Mol. Cell Bio* 2:731-737, (2001).

Takeuchi, et al., "Altered p16/MTSi/CDKN2 and Cycling D1/PRAD-1 Gene Expression Is Associated With The Prognosis of Squamous Cell Carcinoma of the Esophagus" *Clinical Cancer Research* 3:2229-2236, (1997).

Tsujie, et al., "Expression of Tumor Suppressor Gene p16INK4 Products in Primary Gastric Cancer" *Oncology* 58:126-136 (2000).

\* cited by examiner

NIH3T3

CO  E7

← p19

← cdk6

METHOD FOR DETECTING CARCINOMAS IN A SOLUBILIZED CERVICAL BODY SAMPLE

This application is a continuation-in-part of U.S. application Ser. No. 10/633,484, filed Jul. 31, 2003, which claims the benefit to a foreign application EP 02017313.4, filed Aug. 1, 2002.

TECHNICAL FIELD

The present invention relates to a method for the early diagnosis of carcinomas as well as their preliminary stages, particularly carcinomas of the upper respiratory tract or the anogenital tract, from a solubilized body sample.

BACKGROUND OF THE INVENTION

Preventive programs have been offered for the most differing carcinomas since the middle of the fifties. Regarding cervical carcinomas, they are based mainly on the morphological and cytological examination of cytosmears of the cervix uteri, what is called the Pap test, which is made on the basis of gynecological routine examinations at regular intervals in women from the 20th year on. By means of the morphology of the cells, the smears are divided into various intensity degrees of dysplastic cellular changes. According to Pap I-V, these intensity degrees are referred to as normal, mild dysplasia, fairly serious dysplasia, serious dysplasia and invasive carcinoma, respectively. If the Pap test leads to a striking result, a small biopsy will be taken and subjected to a histopathologic examination, by which the kind and intensity of the dysplasia are determined and classified as cervical intraepithelial neoplasia (CINI-III).

In spite of all preventive programs, cervical carcinomas that lead to 400,000 new cases per year are the most frequent carcinomas in women. This is inter alia due to the fact that up to 30% of the results of the Pap test are false-negative.

In conventional screening for cervical carcinoma, swabs are used for detection of neoplastic lesions of the cervix uteri. In the screening procedure, different kinds of lesions have to be distinguished. Causes for lesions may for example be inflammations (due to infectious agents or physical or chemical damage) or preneoplastic and neoplastic changes. In morphological examinations the lesions of different characteristics are sophisticated to distinguish. Thus, for examination of swabs cytologists and pathologists have to be especially trained, and even experienced examiners have a high inter- and intra-observer variance in the assessment of a diagnosis based on cytological specimens. In general, the result of the examination is based upon the subjective interpretation of diagnostic criteria by the examining pathologist/cytologist. As a result, the rate of false positive and false negative results in the screening tests remains unsatisfying high.

However, the reproducibility of the examination results may be enhanced by the use of supporting molecular tools. Yet the problem with the preservation and preparation of the samples may not be overcome by just additionally using molecular markers. One further complication when performing cytological or histological examinations for screening purposes and especially when applying methods for the detection of molecular markers originates from strict precautions in preserving the samples from causing artifacts or improper results.

This is in part due to the instability of the cell-based morphological information and in part to the instability of the molecular markers to be detected during the tests. If the samples are not prepared, transported or stored in an appropriate manner, the cell-based information, or even the molecular information may be lost, or may be altered. So the diagnosis may be impossible, or may be prone to artifacts. For example, the interpretation of biopsies or cytological preparations is frequently made difficult or impossible by damaged (physically or bio-/chemically) cells. Furthermore regarding tissue samples or biopsies, the preservation of molecular constituents of the samples, which are subject to a rapid turnover, is sophisticated due to the time passing by until penetration of the total sample by appropriate preservatives.

As shown above, the morphologically supported diagnostic methods performed routinely in the art show two major disadvantages. Firstly, the methods are highly dependent on individual perception of the examiners. Secondly, the morphological information is quite sensitive to decay processes and thus to production of artifacts after preparation of the samples. Both aspects contribute to improper reproducibility of the results.

Therefore, it is the object of the present invention to provide a method by which cervical carcinomas can be diagnosed early and reliably. In addition, a differentiation should be possible by this method with respect to benign inflammatory or metaplastic changes from dysplastic preneoplasias. Moreover, the present invention provides methods for the detection of carcinomas on a biochemical basis from solubilized samples.

SUMMARY OF THE INVENTION

The present invention is directed to a method for detecting cervical carcinomas, cervical intraepithelial neoplasias, or cervical carcinomas in-situ from a solubilized body sample of a human subject. The method comprises the steps of: (a) obtaining a cervical body sample from a human subject, (b) solubilizing the cervical body sample in a lysis buffer, and (c) determining the overexpression of cyclin dependent kinase inhibitor p16 in the solubilized cervical sample by comparing the level of cyclin dependent kinase inhibitor p16 within said solubilized cervical sample with the level present in a solubilized healthy human cervical sample.

The present invention is also directed to an in-vitro diagnostic device comprising antibodies directed against cyclin dependent kinase inhibitor p16 fixed on solid carriers, for measuring p16 in a solubilized sample.

The present invention is further directed to a test kit for determining the level of cyclin dependent kinase inhibitor p16 comprising antibodies directed against cyclin dependent kinase inhibitor p16 and a lysis buffer for solubilization of a body sample.

DETAILED DESCRIPTION OF THE INVENTION

Figure 1:
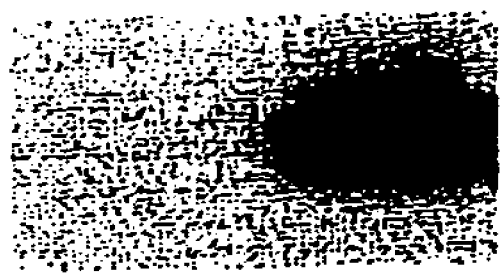
FIG. 1 shows the detection of the overexpression of cdk6 and p19 in HPV16-transformed NIH3T3 cells. The indication co stands for control.
Figure 1:
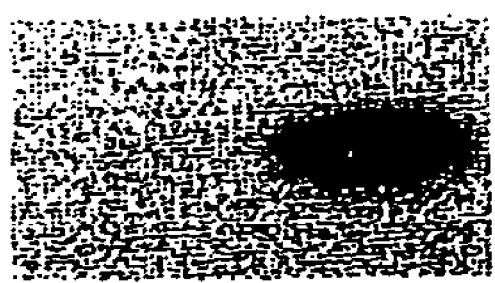

The present invention is based on the applicant's insights that cell cycle regulatory proteins are overexpressed in many carcinomas, e.g. carcinomas of the upper respiratory tract or anogenital carcinomas, particularly cervical carcinoma, and preliminary stages of these carcinomas, respectively. Examples of the cell cycle regulatory proteins are cyclins. Cyclin-dependent kinases which regulate the cyclins are to be mentioned particularly. Cyclin-dependent kinase inhibitors which, in turn, regulate the cyclin-dependent kinases, are to be mentioned even more particularly. Examples of the cyclin-dependent kinase inhibitors are the proteins p14, p15, p16, p19, p21 and p27. The applicant has found that the intensity of cell cycle regulatory protein overexpression correlates with the degree of cell dysplasia.

According to the invention, the applicant's insights are used for a method for the early diagnosis of carcinomas and their preliminary stages, which comprises determining the overexpression of cell cycle proteins in a body sample.

According to the invention, cytological or histological examination procedures may be substituted by the use of molecular markers. Such markers may e.g. be used in immuno-histochemical staining reactions, or in the course of in-situ hybridization reactions. Combinations of morphological examinations and immuno-histochemical staining reactions based on marker molecules, characteristic for carcinoma of the cervix uteri, may lead to enhanced results. The morphologic examination remains laborious and time consuming and thus expensive, even when supported by the molecular methods, that make the results more reliable. Additionally, the diagnosis on a morphologically cell based level is, even when supported by molecular parameters, subject to individual perception of the morphology by individual examiners. Thus the diagnosis is dependent on the person, that performs the examinations.

The inventors moreover could show that in specific cases molecular markers may be used as diagnostic tools without further support by cell based morphological examinations. Methods for diagnosis of carcinomas on a molecular level only, without the support of cell based information, are restricted to cases, where markers or levels of markers are non-ambiguously specific for the condition to be characterized. This is especially true, if the markers are non-human substances. For example detection of viral infections may be carried out in solutions of samples, because the markers characteristic for the presence of viruses in tissues do not occur in unaffected human tissues.

However, the inventors found that human cyclin dependent kinase inhibitor p16 may serve as a marker for carcinomas in biochemical marker based detection procedures although it is a cell cycle regulatory protein being expressed at low levels in any normally proliferating human cell in certain stages of the cell cycle.

"p16" or "cyclin dependent kinase inhibitor p16" as used herein refers to cyclin dependent kinase inhibitor p16INK4a (also denominated as CDKN2 or MTS1) the gene of which is located in chromosomal region 9p21. p16 was first described in Serrano, M., et al., Nature, 1993 Dec. 16; 366(6456):704-7. The terms "p16" or "cyclin dependent kinase inhibitor p16" in all their grammatical forms as used in the context of the present invention refers to nucleic acid as well as polypeptide molecules. "p16" or "cyclin dependent kinase inhibitor p16" thus comprises e.g. RNA (mRNA, hnRNA, etc.), DNA (cDNA, genomic DNA, etc.), proteins, polypeptides, proteoglycans, glycoproteins and the respective fragments of these molecules.

The level of p16 refers to a semiquantitave as well as a quantitative value regarding the amount of the p16 present in a sample. A quantitative value may e.g. be represented in terms of a concentration. A semiquantitative value may be expressed in terms of a scale of levels e.g. undetectable levels, low levels, intermediate levels, high levels or any other suitable mode. The level of p16 may also be represented in terms of a dependent parameter such as the intensity of a signal generated in an assay format in response to the presence of p16. In certain embodiments the level of p16 may also refer to a qualitative determination of the presence of p16.

Due to the expression of cyclin dependent kinase inhibitor p16 in certain benign cell types present in cervical specimens, the diagnosis of dysplasias based on the level of cyclin dependent kinase inhibitor p16 without additional information on the cellular morphology seem to be difficult or impossible. It was known in the art that up to 30% of metaplastic cells, which may be present in cervical swabs, are immunoreactive for cyclin dependent kinase inhibitor p16 at a moderate to high level. Moreover, endometrial cells that may under certain circumstances be present in cervical swabs are positive for p16. In cytological or histological testing procedures, this fact does not influence the diagnosis, because the cell types may easily be distinguished from dysplastic cells with respect to their cellular morphology.

Surprisingly the inventors found that by defining a threshold value of cyclin dependent kinase inhibitor p16, it is possible to enable the detection or diagnosis of dysplasias even without knowledge of the cellular morphology.

The expression "carcinomas and their preliminary stages" comprises carcinomas of any kind and origin and preliminary stages thereof, respectively. For example, they may be carcinomas of the upper respiratory tract or anogenital carcinomas, particularly the cervical carcinoma. In connection with the latter, its preliminary stages, e.g. cervical intraepithelial neoplasias (CIN I-III), carcinomas in situ (CIS, locally restricted carcinomas, not beyond the basal lamina of the epithelium), etc., have to be mentioned particularly. Preliminary stages as used herein comprises all precursor stages and precursors of carcinomas or any other malignancies. With respect to cervical carcinoma precursory or preliminary stages as used herein may e.g. refer to stages of cervical intraepithelial neoplasias as identified by appropriate classification systems such as e.g. the CIN classification (CIN I-CIN III) the PAP classification (PAP I-PAP V) or the Bethesda Classification (LSIL, HSIL).

The expression "cell cycle regulatory proteins" comprises cell cycle regulatory proteins of any kind and origin. For example, the proteins may be cyclins. In particular, they may be cyclin-dependent kinases which regulate the cyclins. Examples of the cyclin-dependent kinases are the proteins cdk4 and cdk6. More particularly, they may be cyclin-dependent kinase inhibitors which, in turn, regulate the cyclin-dependent kinases. Examples of cyclin-dependent kinase inhibitors are the proteins p14, p15, p16, p18, p19, p21 and p27, with p16 being preferred.

The expression "body sample" comprises any body samples in which cell cycle regulatory proteins can be detected. Examples of such body samples are secretions, swabs, lavages, body fluids, semen, cell- and tissue-samples, blood, smears, sputum, urine, stool, liquor, bile, gastrointestinal secretions, lymph, bone marrow, aspirates and biopsies of organs such as needle or punch biopsies and (fine)-needle aspirates. In particular, smears, swabs and biopsies are indicated when the detection of anogenital carcinomas, e.g. cervical carcinomas, is concerned. Biopsies as used in the context of the present invention may comprise e.g. resection samples of tumors, tissue samples prepared by endoscopic means or punch- or needle-biopsies of organs.

Body samples as used in the context of the present invention may comprise fixed or preserved cell or tissue samples. Cell or tissue samples may e.g. be preserved in a standard sample collection, storage or transportation solution, known to those of skill in the art such as e.g. commercially available preservation solutions (formalin solution, Cytyc "PreserveCyt", Digene "Universal Collection Medium", Tripath "Cytorich", etc.). Those solutions may contain one or more alcohols, aldehydes, ketones, acids, metal-ions or sublimates, ethers etc. for preservation of cellular components. Alcohols include methanol, ethoanol, (n- or i-) propanol, (n-, i- or t-) butanol or higher branched or unbranched alcohols. Aldehydes include formaldehyde, acetaldehyde, glutaraldehyde, etc. Ketones such as Acetone may be used. Acids for use in standard sample solutions include organic acids (acetic acid, trichloro-acetic acid, salicylic acid, picrinic acid) or inorganic acids such as chromic acid. Standard sample solutions may comprise metals such as silver, copper, chromium, mercury, osmium, uranium. Solutions of salts such as uranyl-acetate, potassiumbichromate, ammonium sulfate, etc. may be components of preservative solutions.

Cells preserved in suitable solutions (alcohols etc.) or fixed tissue samples may be used as raw samples in the methods according to the present invention. In one embodiment, the body sample may e.g. comprise a cervical swab, that has been transferred to a preservative solution containing alcohol. Furthermore, body samples that have been subjected to cell lysing conditions immediately after obtaining the samples may be used in the methods disclosed herein.

Applicant has found a number of robust, fast and easy ways to preserve molecular properties of samples, in which the morphological information of samples is lost. Samples may be e.g. prepared in a reproducible and easy to store and to transport form by dissolving the cellular components of the raw sample in a suitable solvent immediately after or even during obtaining the sample. Body fluids may directly be transferred from the body of an individual to a solution containing suitable detergents and preservative substances. Furthermore, tissue samples may immediately be transferred to denaturing lysis conditions (eventually supported by physical forces) and be thus preserved. Using appropriate ingredients in the solvent, the molecular components of the original sample may be preserved, and no degradation may occur. The degradation by enzymatic activities may for example be minimized by the use of enzyme inhibitors. Thus, a solution of test samples may represent the molecular properties of a test sample at the time of dissolution.

According to the present invention, the body samples may be solubilized in any suitable solvent. Such solvents may for example be aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), nonionic detergents (e.g. TWEEN®-20, polyethylene glycol sorbitan monolaurate; nonidet P-40, TRITON® X-100, t-octylphenoxypolyethoxyethanol; NP-40, IGEPAL® CA 630, nonidet P 40; N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH. Generally any suitable liquid may be used as a solvent in the lysis buffer of the present invention. The liquid may be organic or inorganic and may be a pure liquid, a mixture of liquids or a solution of substances in the liquid and may contain additional substances to enhance the properties of the solvent. In certain embodiments, where lysis of cells may be achieved without the use of detergents, hyper- or hypotonic solutions or buffers or simply water or an organic liquid may be used as solvent. Any liquid that is suited to solubilize the cellular components of body samples in total or in parts may be regarded as a lysis buffer as used herein. Thus lysis buffers as used herein need not contain buffer substances or have buffer capacity.

In one embodiment, the solvent is designed, so that cells, cell debris, nucleic acids, polypeptides, lipids and other biomolecules potentially present in the raw sample are dissolved. In further embodiments of the present invention, the solvent may be designed to assure differential lysis of specific components of the body sample, leaving other components undissolved.

The solution for dissolving the body sample according to the present invention may furthermore comprise one or more agents that prevent the degradation of components within the raw samples. Such components may for example comprise enzyme inhibitors such as proteinase inhibitors, RNAse inhibitors, DNAse inhibitors, etc. In one embodiment of the present invention, the sample is lysed directly in the form obtained from test-individuals. Proteinase inhibitors may e.g. comprise inhibitors of serine proteinases, inhibitors of cysteine proteinases, inhibitors of aspartic proteinases, inhibitors of metally proteinases, inhibitors of acidic proteinases, inhibitors of alkaline proteinases or inhibitors of neutral proteinases.

In another embodiment of the present invention the body sample may be further purified before being lysed. Such purification procedures may for example comprise washing away of contaminants such as mucus or the like, separation or concentration of cellular components, preserving and transporting of the cells. Thus the cellular components of the raw samples are included in a single sample solution.

The preparation of a sample for use in a method as disclosed herein may also comprise several steps of further preparations of the sample, such as separation of insoluble components, isolation of polypeptides or nucleic acids, preparation of solid phase fixed peptides or nucleic acids or preparation of beads, membranes or slides to which the molecules to be determined are coupled covalently or non-covalently.

The expression "determining the overexpression of cell cycle regulatory proteins" comprises any methods which are suited for detecting the expression of cell cycle regulatory proteins or their encoding mRNAs and an amplification of the corresponding genes, respectively. In order to determine an overexpression, the body sample to be examined is compared with a corresponding body sample which originates from a healthy person. Such a sample can be present in a standardized form.

The comparison with normal healthy body samples may be achieved by different methods. In one embodiment of the present invention, the comparison may be performed directly by including a control reaction with non-diseased tissue or cell sample. This non-diseased tissue or cell samples may be provided from a healthy person or from non-diseased regions of the human subject under examination or from cell culture cells known to show the properties of non-diseased cells with respect to cyclin dependent kinase inhibitor p16 expression. In another embodiment, the comparison may be performed indirectly by comparing the level of cyclin dependent kinase inhibitor p16 within the sample under investigation to a level of cyclin dependent kinase inhibitor p16 known to be present in normal healthy samples. The knowledge about the level for normal healthy tissue or cell samples may be derived from a representative number of testing or from scientific publication providing information the expression level of cyclin dependent kinase inhibitor p16 in normal healthy cells. Comparison may be performed by employing a value for the concentration of the p16 protein or nucleic acids; otherwise a characteristic value depending on the protein or nucleic acid concentration such as the optical density under defined reaction conditions may be employed. Otherwise the known value may be represented by a surrogate control such as a peptide or a recombinant protein. Thus the level of p16 present in normal healthy samples may be represented by a control sample of a recombinant protein or a peptide in the testing procedure.

Generally, the comparison of the level present in the sample under investigation may be performed with respect to a value determined in each single testing procedure or to a predetermined value. The predetermined value may be determined for the testing procedure globally. Otherwise, the value may be valid only for a certain lot of testing reagents. For example, the reference value may be valid for a defined calibration period only and may be defined upon calibration of the testing process.

The level of p16 in a healthy human cervical sample can be determined from a standardized sample solution. A standardized sample solution may comprise a solution of a solubilized pool of normal cell or normal tissue samples. The sample pool may, e.g., be a pool of cytological specimens with pre-assessed normal diagnosis from a screening population, or a pool of normal cells obtained from histological specimens. Furthermore, a pool of normal cells may be obtained from tissue culture of normal cervical epithelial cells. The sample solution may, e.g., be standardized with respect to the content of cells per ml sample solution. Any other parameter for standardization may be applied. The sample solution may e.g. be provided in a standardized form to ensure stability and reproducibility of the test results. In certain embodiments such solution may be provided as a component of the kit for comparison or calibration purposes.

In certain embodiments, the step of comparing the level of cyclin dependent kinase inhibitor p16 present in a patient sample to a level known to be present in a normal healthy body sample is embodied as employing a cut-off value or threshold value for the concentration of p16. The cut-off in this context is a value (e.g. for the concentration of p16 protein given in e.g. mg/ml or for the optical density measured under defined conditions in an ELISA test) which is suited to separate normal healthy samples from diseased samples. e.g. all samples giving values above the cut-off value are considered to be dysplastic, whereas the samples giving value below the cut-off value are considered to be healthy.

In certain embodiments, the threshold or cut-off may be set in a way to separate high grade dysplasias from all less severe stages of dysplasias. In other embodiments, the cut-off may be defined to differentiate healthy samples from dysplasias including precursory stages. It is thus possible to tailor the testing format in order to fit different tasks such as early detection of lesions and even precursors of the lesions or detection of lesions that deserve immediate therapy.

The (over) expression of cell cycle regulatory proteins can be detected on a nucleic acid level and protein level, respectively. Regarding the detection on a protein level, it is possible to use e.g. antibodies which are directed against cell cycle regulatory proteins. These antibodies can be used in the most varying methods such as Western blot, ELISA or immunoprecipitation. It may be favorable for the antibodies to be fixed on solid carriers such as ELISA plates, reaction vessels, beads, spheres, membranes, colloidal metals (e.g. gold), porous members, surfaces of capillaries (e.g. in flow through test), test strips or latex particles.

In certain embodiments of the present invention, the detection of the marker molecules is performed from a solution of dissolved body samples. Therefore detection may be carried out in solution or using reagents fixed to a solid phase.

A solid phase as used in the context of the present invention may comprise various embodiments of solid substances such as planar surfaces, particles (including micro-, nano-particles or even smaller particles). In certain embodiments, particles may be provided as spheres, beads, colloids, or the like.

The fixation of reagents to the solid phase in a test kit or an in-vitro diagnostic device may be carried out via direct fixation or via indirect fixation. Direct fixation may be carried out by covalent binding, non-covalent binding, association, or adsorption to surfaces. Indirect fixation may be carried out through binding of the antibody to agents which themselves are directly fixed to solid phases. Binding agents, for example, include avidin, streptavidin, biotin, digioxingenin, antibodies or the like.

The detection of one or more molecular markers may be performed in a single reaction mixture or in two or more separate reaction mixtures. The detection reactions for several marker molecules may for example be performed simultaneously in multi-well reaction vessels. The detection reaction for marker molecules may comprise one or more further reactions with detecting agents either recognizing the initial marker molecules or preferably recognizing the prior molecules (e.g. primary antibodies) used to recognize the initial markers. The detection reaction further may comprise a reporter reaction indicating the level of the markers characteristic for cell proliferative disorders or the normalization markers.

The detection reaction for detecting the level of cyclin dependent kinase inhibitor p16 in solubilized samples may be carried out in solution or with reagents fixed to solid phases. In certain embodiments, the detection reaction may be carried out in solution; such procedures may comprise any methods suited for the detection of molecular interactions (binding of an antibody or similar binding agent to an antigen) in solution. The methods for determination of molecular interaction (change in conductivity, mass changes, light-, UV-, IR-, magnetic spectrometric changes, plasmon resonance, etc.) are known to those of skill in the art. In certain embodiments the detection may comprise a method where a complex of detection reagent bound to antigen is adsorbed to a solid phase for detection purpose. Thus, non-covalent bonding of the analytes to solid phases in the course of the detection reaction or even before starting the detection reaction may be used in a method according to the present invention.

A probe for the detection of the marker molecules may be any molecule, that specifically binds to said marker molecules. The probe may for example be an antigen binding agent such as antibodies (monoclonal or polyclonal), antibody fragments or artificial molecules comprising antigen binding epitopes, DNA or RNA binding molecules such as proteins or nucleic acids. Nucleic acids binding to other nucleic acids may for example be oligonucleotides for detection purposes or primers. A molecule is said to recognize another molecule if it specifically interacts with that molecule. Specific interaction may for example be specific binding to or of the other molecule. The term "antibody" in all its grammatical forms shall in the context of the present invention refer generally to antigen binding molecules including but not limited to monoclonal and polyclonal antibodies, fragments of antibodies, antigen binding epitopes, mini-antibodies, peptidomimetics with antigen-binding properties, anticalines and diabodies.

The reporter reaction may be any event producing a signal in response to the presence of the marker or to the binding of a specific probe to the marker. For example, a reaction producing a colored compound, a fluorescent compound, a light emitting compound, a radiation emitting compound, or the concentration of one or more of these compounds to a detectable concentration in a predefined area of a testing device may serve as reporter reaction.

Applicable formats for the detection reaction according to the present invention may be blotting techniques, such as Western-Blot, Southern-blot, Northern-blot. The blotting techniques are known to those of ordinary skill in the art and may be performed for example as electro-blots, semidry-blots, vacuum-blots or dot-blots. Furthermore immunological methods for detection of molecules may be applied, such as for example immunoprecipitation or immunological assays, such as EIA, ELISA, RIA, FIA (fluorescent immunoassay) lateral flow assays (using porous members or capillaries), immunochromatographic strips, flow through assays, latex agglutination assays etc. In nucleic acid based approaches hybridization or amplification techniques may be applied.

Immunoassays for use in the invention may comprise competitive as well as non-competitive immunoassays, such as sandwich assays.

In certain embodiments of the invention, immunochemical or nucleic acid based testing may be performed using a testing device for clinical laboratories. Such testing device may comprise any device suitable for immunochemical or nucleic acid based testing including any format such as point of care testing devices as well as bench top or laboratory devices. The devices may be e.g. provided as open or closed platform systems. The system may be based on any suitable methodology such as microtiter plates, multiwell plates, flow through or lateral flow systems, microchip or array based systems or bead or membrane based systems. The detection methods employed may comprise any methods known to those of skill in the art useful for immunochemical or nucleic acids based detection reactions. Such detection systems may be e.g. luminescence systems (electroluminescence, bioluminescence, photoluminescence, radioluminescence, chemiluminescence, electrochemoluminescence), fluorescence based systems, conductivity based detection systems, radiation (light, UV, X-ray, gamma etc.), plasmon resonance (e.g. Surface Plasmon Resonance SPR) or any other known method.

The term porous member as used herein shall generally apply to any three dimensional arrangements of porous substances. Such porous member may e.g. comprise compounds as membranes, beads or other.

By means of the present invention it is possible to diagnose carcinomas early, i.e. in their preliminary stages.

A further subject matter of the present invention relates to a kit for carrying out a method according to the invention. Such a kit comprises e.g.:

(a) a reagent for detecting the expression of a cell cycle regulatory protein, e.g. an antibody directed against such a protein or a nucleic acid coding for such a protein and parts thereof, respectively,
(b) a lysis buffer for solubilization of the body sample,
(c) conventional auxiliary agents, such as buffers, carriers, markers, etc., and optionally
(d) an agent for control reactions, e.g. a cell cycle regulatory protein, a nucleic acid coding for such a protein and parts thereof, respectively, or a preparation of cells.

Furthermore, one or several of the individual components may be present. For example, the detection reagent and as other reagents fixed to a solid phase may be present.

Generally, the lysis buffer may be any suitable solvent known to those of skill in the art. The lysis buffer for use in the kit may, for example, be organic or aqueous solutions of chaotropic agents such as e.g. urea, GuaSCN, Formamid, of detergents such as anionic detergents (e.g. SDS, N-lauryl sarcosine, sodium deoxycholate, alkyl-aryl sulphonates, long chain (fatty) alcohol sulphates, olefine sulphates and sulphonates, alpha olefine sulphates and sulphonates, sulphated monoglycerides, sulphated ethers, sulphosuccinates, alkane sulphonates, phosphate esters, alkyl isethionates, sucrose esters), cationic detergents (e.g. cetyl trimethylammonium chloride), non-ionic detergents (e.g. TWEEN® 20, nonidet P-40, TRITON® X-100, NP-40, IGEPAL® CA-630, N-Octyl-Glucosid) or amphoteric detergents (e.g CHAPS, 3-Dodecyl-dimethylammonio-propane-1-sulfonate, Lauryldimethylamine oxide) and/or of alkali hydroxides such as e.g. NaOH or KOH. In certain embodiments, where lysis of cells may be achieved without the use of detergents, hyper- or hypotonic solutions or buffers or simply water or an organic liquid may be used as solvent. Any liquid, that is suited to solubilize the cellular components of body samples in total or in parts may be regarded as a lysis buffer as used herein. Thus, lysis buffers as used herein need not contain buffer substances or have buffer capacity.

To obtain optimal results of the assay, the pH of a lysis buffer that can be directly applied to the assay system is around neutral. The pH of the lysis buffer is within the range of 4 to 10. In certain embodiments, the pH is in a range from 5 to 9. In a preferred embodiment, the pH is in a range from 6 to 8. In a more preferred embodiment, the pH is in the range from 6.5 to 7.5.

Examples of Lysis Buffers may, for example, be selected from the compositions given in Table 1.

TABLE 1

| Lysis buffer | solubilization of p16INK4a in Western blot | compatibility with Elisa |
|---|---|---|
| Detergents: | | |
| 0.1-1% SDS | + | +/− |
| 0.2-3% SDS | + | <0.5% |
| 0.2-3% DOC | ++ | +/− |
| 0.1-1% n-Octylglycoside | + | yes |
| 0.1-3% TRITON ® X-100 | + | yes |
| 0.1-1% Chaps | + | nd |
| Detergent-Mix: | | |
| RIPA (1% NP40, 0.5% DOC, 0.1% SDS, PBS) 40-100% | ++ | yes |
| SOX (0.5% DOC, 0.5% n-Octylglycoside) 40-100% | + | yes |
| mtm lysis buffer (3% TRITON ® X-100, 0.4% SDS, PBS) | ++ | yes |
| Commerical lysis buffers: | | |
| Dynal (Dynal, Oslo, Norway) | ++ | yes |
| M-PER/B-PER (Pierce, Rockford, IL) | ++ | yes |
| Miscellaneous: | | |
| 0.5-8 M urea in PBS | +++ | Compatible < 2 M |
| Lämmli sample buffer | +++ | no |
| 10-80% DMSO | +++ | no |
| 10-80% Formamide | nd | no |
| 50-70% formic acid | ++ | no |
| PBS | +/− | yes |
| Citrate buffer pH 6.0 | +/− | yes |
| 500 mM NaCl in Phosphate buffer | +/− | yes | nd: not determined;
+/−: poor;
+: good;
++: very good;
+++: excellent;

In certain situations, the cyclin dependent kinase inhibitor p16 can be degraded in the solubilized samples and may thus not be detected. This is particularly true, if the samples are directly transferred to a lysing medium and stored therein for a certain period of time. To prevent degradation, lysis buffer may furthermore comprise one or more agents that prevent the degradation of components within the raw samples. Such components may for example comprise enzyme inhibitors such as proteinase inhibitors, RNAse inhibitors, DNAse inhibitors, etc. The inhibitors may e.g. comprise proteinase inhibitors selected from the compositions given in Table 2.

TABLE 2

| Inhibitor | class of inhibited proteinase | concentration | Solubility in water | stability in water | p16 stabilization in mtm lysis buffer |
|---|---|---|---|---|---|
| Aprotinin | Serine | 0.6-2 µg/ml | Very good | good | no |
| Benzamidine | Serine | 0.5-4 mM | good | good | no |
| Bestatin | Aminopeptidases | 1-10 µM | good | good | no |
| Calpeptin | Cysteine | 0.3-1 µM | good | good | no |
| Cystatin | Cysteine | 1 µM | good | good | no |
| E-64 | Cysteine | 1-10 µM | good | good | no |
| EDTA | Metallo | 0.5-5 mM | good | good | no |
| Elastatinal | Serine | 0.5-2 µg/ml | poor | good | no |
| EST | Cysteine | 20-50 µg/ml | bad | poor | no |
| Fetal calf serum | all classes | 10% | good | good | yes |
| Leupeptin | Serine/Cysteine | 10-100 µM | good | good | no |
| a2-Macroglobulin | all classes | 1 µM | good | good | no |
| NCO-700 | Cysteine | 0.5-100 mM | poor | poor | no |
| Pefabloc = AEBSF | Serine | 0.2-10 µM | good | very poor | yes |
| Pepstatin A | Aspartic | 1 µM | bad | poor | no |
| PMSF | Serine | 0.2-10 µM | bad | very poor | yes |
| o-Phenanthroline | Metallo | 1-10 mM | bad | poor | no |

For stabilization purpose, the lysis buffer may also comprise bulk protein (e.g. albumin such as bovine serum albumin or calf serum albumin or other bulk proteins) to compete in degradation with the sample proteins. The bulk proteins may e.g. be present in combination with proteinase inhibitors or may be added instead of proteinase inhibitors. In one embodiment, the solvent may be selected to be compatible with the assay (e.g. ELISA) performance, so that solubilized samples may directly be applied to the assay.

In some embodiments of the present invention, the lysis buffer may be tailored in order to enable for the setting of a specific cut-off value.

One aspect of the invention relates to an in-vitro diagnostic device. An in-vitro diagnostic device according to the present invention is characterized by solid phase fixed detection reagents specific for a cyclin dependent kinase inhibitor. In one embodiment, the detection reagents are specific for cyclin dependent kinase inhibitor p16.

In the art, there are some in-vitro diagnostic devices employing reagents for the detection of cyclin dependent kinase inhibitor p16 in histological or cytological specimens. These in-vitro diagnostic devices are cell-based detection devices that detect the p16 antigen in cells or tissues, not in solubilized samples.

p16 being an intracellular antigen, it may only be accessible to detection reagents in solution after permeabilization of cells. Thus, the in-vitro diagnostic application of reagents for detection of cyclin dependent kinase inhibitor p16 known in the art excludes the fixation of the detection reagents to a solid phase. The art have not taught the design of test kits or in-vitro diagnostics containing p16-fixed solid phase detection reagents. An approach for assessing diagnosis on the basis of solubilized samples seemed not viable from the art and has not been suggested before.

It is thus an aspect of the present invention to provide an in-vitro diagnostic device comprising probes directed against cyclin dependent kinase inhibitor p16$^{INK4a}$ fixed to a solid phase allowing assessment of diagnosis of carcinomas and their precursor lesions in a solubilized sample. In certain embodiments of the present invention, the probes may e.g. comprise antibodies or fragments thereof directed against p16$^{INK4a}$ protein. It is an advantage of the in-vitro diagnostic devices of the present invention to allow for easy and economic assessment of diagnosis of carcinomas and their precursor lesions. The test may be suited for screening purposes as well as for diagnostic purposes and may be applied in primary diagnosis as well as in monitoring of disease course. The in-vitro diagnostic devices may in certain embodiments be applicable for use in clinical laboratories, for point of care testing or even for self testing.

The in-vitro diagnostic devices comprising solid phase fixed reagents for the detection of cyclin dependent kinase inhibitor p16 may be useful for the detection of various different carcinoma-entities and their respective precursor lesions. The in-vitro diagnostic devices may be applied for analysis of any kind of lysed body samples.

The antibodies can be fixed to the solid phase via direct fixation or via indirect fixation. Direct fixation can be done by covalent or non-covalent binding or association to surfaces. Indirect fixation can be done through binding of the antibody to agents which themselves are directly fixed to solid phases. Such agents may comprise antibodies or other binding agents like avidin, streptavidin, biotin, digioxingenin or the like.

The in-vitro diagnostic devices envisaged in the invention are selected from the group consisting of
 a. an ELISA device comprising antibodies directed against cyclin dependent kinase inhibitor p16 fixed to ELISA plates, ELISA stripes or ELISA wells;
 b. a lateral flow test device, comprising antibodies directed against cyclin dependent kinase inhibitor p16 fixed to test strips, colloidal gold particles or latex particles;
 c. a flow through assay device, comprising antibodies directed against cyclin dependent kinase inhibitor p16 fixed to a porous member, or to the surface of capillaries;
 d. a latex agglutination assay device, comprising antibodies directed against cyclin dependent kinase inhibitor p16 fixed to latex particles; and
 e. an immunoassay device, comprising antibodies directed against cyclin dependent kinase inhibitor p16 fixed to beads, membranes, or microspheres.

The ELISA devices may be of any kind known to those of skill in the art. These devices comprise devices for sandwich ELISA formats, for competitive ELISA formats and any other ELISA formats.

Lateral flow assay devices for use as an in-vitro diagnostic device according to the present invention are any lateral flow assay devices employing at least one reagent binding to cyclin dependent kinase inhibitor p16 fixed to a solid phase. Such devices may employ various mechanisms for visualization of the test result. In certain embodiments, the tests may employ secondary detection reagents directed against cyclin dependent kinase inhibitor p16 or another component participating in the test couples to detectable moieties. The detectable moieties may comprise colloidal gold, (colored) latex particles and others.

Flow through assay devices for use in the present invention may comprise devices based on capillaries or on porous members (such as membranes, beads or other three dimensional arrangements of porous substances). Depending on the embodiment the size of pores or capillaries need to adjusted to ensure optimal flow conditions.

By means of the present invention, it is possible to diagnose carcinomas early. In particular, preliminary stages of carcinomas can be detected early. It must also be emphasized that it is possible to make a differentiation with respect to benign inflammatory or metaplastic changes of dysplastic preneoplasias. Another characteristic is that the results obtained by a method according to the invention are not subject to a subjective evaluation, so that e.g. false-negative results and false-positive results of a Pap test or histological preparations can be avoided. In addition, the present invention distinguishes itself by rapid and simple handling, so that it can be used for extensive screening measures, particularly also in third-world countries. Thus, the present invention represents an important contribution to today's diagnostics of cancerous diseases.

The invention is illustrated further by the following examples, which are not to be construed as limiting the invention in scope or spirit to the specific procedures described in them.

EXAMPLES

Example 1

Detection of the Overexpression of p16 in Biopsies of the Cervix Uteri (A) Paraffin sections having a thickness of 3 to 5 µm were produced from 20 biopsies of the cervix uteri, which comprised all degrees of the dysplastic progression from normal tissue (n=2) via CIN I (n=4), II (n=4), III (n=5) lesions to the invasive carcinoma (n=5). They were deparaffinized in xylene for 2×10 min. and rehydrogenated using ethanol. The antigens were demasked in 10 mM citrate buffer (pH 6.0) in an autoclave at 110° C. for 10 min. Thereafter, the endogenous peroxidases were inactivated using 0.25% H2O2 in PBS. Following the blocking of unspecific binding sites with horse serum (Vectastain ABC detection kit, Vector Laboratories, Burlingame, Calif.) at room temperature for 20 minutes, the sections were incubated with a p16-specific monoclonal antibody (Neomarkers, Fremont, Calif.) in the presence of 3% fetal calf serum at room temperature for 45 min. For the detection of the p16-antibody binding, a biotinylated secondary antibody (horse anti-mouse IgG, Vectastain kit, see above) was then added for 30 minutes. Thereafter, the bound secondary antibody was detected by means of the reagents and in accordance with the Vectastain kit instructions and a core counterstain was carried out using Mayer's hemalum solution.

It shows that an overexpression of p16 exists in dysplasia cells. It also shows that the intensity of p16 overexpression correlates with the degree of cell dysplasia.

(B) In addition, paraffin sections were prepared from 78 biopsies of the cervix uteri. The biopsies relate to normal tissue (n=12), dysplastic lesions of stages CIN I (n=15), II (n=14) and III (n=18) as well as invasive carcinomas (n=19). The paraffin sections were treated as described in (A). The data indicated in Table 3 were obtained.

TABLE 3

| | | p 16 expression intensity | | | |
|---|---|---|---|---|---|
| histology | n= | – | + | ++ | +++ |
| normal | 12 | 9 | 3 | | |
| CIN I | 15 | 10 | 3 | 2 | |
| CIN II | 14 | 1 | 4 | 9 | |
| CIN III | 18 | | | 9 | 9 |
| CxCa | 19 | | | 1 | 18 |
| total | 78 | 20 | 10 | 21 | 27 |

Table 3 shows that p16 is overexpressed in cells of dysplasias and invasive carcinomas, the overexpression increasing with the degree of dysplasia towards the invasive carcinoma.

(C) Moreover, paraffin sections from 180 biopsies of the cervix uteri were treated as described in (A). In addition, the percentage cell number is determined which reacts with the above-mentioned p16-specific monoclonal antibody. A distinction is also made between HPV-positive and HPV-negative dysplasias and invasive carcinomas, respectively. The data indicated in Table 4 were obtained.

TABLE 4

| | Percentage of cells overexpressing p16 | |
|---|---|---|
| | n | average percentage + standard deviation |
| CIN I | 32 | 54.9 + 24.0 |
| HPV-negative | 17 | 54.0 + 27.2 |
| HPV-positive | 15 | 55.9 + 21.0 |
| CIN II | 32 | 70.8 + 18.9 |
| HPV-negative | 14 | 76.0 + 15.8 |
| HPV-positive | 18 | 66.8 + 20.5 |
| CIN III | 60 | 92.4 + 10.2 |
| HPV-negative | 9 | 94.4 + 7.5 |
| HPV-positive | 51 | 92.1 + 10.7 |
| Invasive carcinoma | 58 | 97.8 + 5.2 |
| HPV-negative | 5 | 96.4 + 8.1 |
| HPV-positive | 53 | 97.9 + 4.9 |

The data of Table 4 disclose that p16 is overexpressed in both HPV-positive cells and HPV-negative cells of dysplasias and invasive carcinomas. This result is confirmed by controls with normal tissue. The data also show that the percentage of cells reacting with p16 increases with the degree of dysplasia towards the invasive carcinoma.

Example 2

Detection of the Overexpression of Cell Cycle Regulatory Proteins in HPV-transformed Cells (A) Cervical carcinoma cells CaSki which had been transformed with HPV16 were cultured in the absence of serum for 72 h. Following the addition of serum, cell extracts were collected at various times, subjected to SDS-PAGE and transferred to PVDF membranes (Du Pont). The expression of cdk4 was determined using polyclonal antiserum (1:1000) from Santa Cruz. Furthermore, the expression of HPV16-E7 protein was determined with a monoclonal antibody against HPV16-E7 (1:50) from Triton. The individual immune responses were detected via peroxidase-linked second antibodies and a chemiluminescence detection system (NEN, Du Pont).

FIG. 1 shows that cdk4 was overexpressed.

(B) NIH3T3 cells were transformed with HPV16 so as to obtain an expression of HPV16-E7 protein. Cell extracts of the transformed cells were obtained and treated as described in (A). For detecting the expression of cdk6 and p19, respectively, polyclonal antisera (1:1000) from Santa Cruz were used. As far as the detection of the expression of HPV16-E7 protein and the detection of the individual immune responses are concerned, reference is made to the above statements under item (A).

Figure 2:
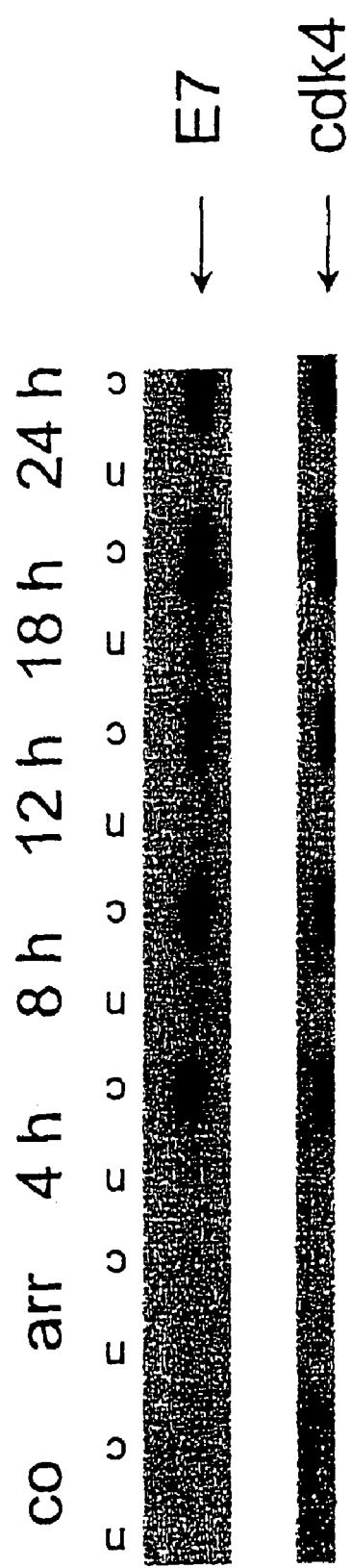
FIG. 2 shows the detection of the the cdk4 overexpression in HPV16-transformed cervical carcinoma cells CaSki. The indications 4 h, 8 h, 12 h, 24 h refer to the times of cell extract removal. The indication co stands for control while arr indicates the addition of the serum.

FIG. 2 shows that cdk6 and p19 were overexpressed.

Example 3

Detection of Cervical Intraepithelial Neoplasia in an ELISA Test Format 33 cervical swabs provided in a lysis buffer were subjected to ELISA based detection of overexpression of cyclin dependent kinase inhibitor p16 in solutions prepared from the cells contained in the swabs. The ELISA testing was performed as follows:

(A) Cell Lysis

Cervical swab brushes were given into 15 ml vessels, containing 2 ml of mtm lysis buffer (2% TRITON® X-100, 0.4% SDS, 0.6 mM PMSF in PBS). Cervical cells present in the brush were lysed for at least 20 h. The lysates of the cervical swab samples were then transferred in 2 ml tubes and were centrifuged at 4° C. (15 min at 28.000×g (16.600 rpm HighspeedCentrifuge JEC Multi RF)); Supernatant was transferred to a fresh tube. The supernatant may be stored at −20° C.

(B) Performing the ELISA

Coating of ELISA-plates

Stock-solution of p16 specific antibody clone mtm E6H4 was diluted in PBS to give ready-to-use coating solution.

50 µl of the coating solution was added to each well of the ELISA plates.

For coating, the plates were incubated overnight at 4° C.

Coating solution was removed from the ELISA plates and the plates were rinsed using an automated ELISA washer as follows:

7×250 µl washing buffer (0.1% TWEEN® 20 (v/v) in PBS) after removing remnants of the washing buffer, 300 µl blocking buffer (2% BSA in PBS) was added to each well. Plates were incubated for 1 h on a rocking device at ambient temperature.

Incubation with Samples

After removing the blocking buffer, 100 µl of the lysed cell sample was added to each well. Lysates of HeLa-cells were used as positive control;

For purpose of calibration of the test, different concentrations of recombinant p16 protein (0 pg/ml, 50 pg/ml, 100 pg/ml, 200 pg/ml, 400 pg/ml, 800 pg/ml) were included in the test.

Samples were incubated for 1 h at room temperature.

Thereafter washing was performed on an automated ELISA washer as follows:

7×250 µl washing buffer. The remaining buffer was removed.

Incubation with Detection Antibody

Working solution of biofinylated secondary antibody clone mtm D7D7 specific for p16 protein was prepared by dilution of stock solution.

100 µl of working solution was added to each well. After incubation for 1 h at RT, antibody solution was removed and ELISA plates were washed by an automated ELISA washer 7× with 250 µl washing buffer.

Detection

Streptavidin-HRP-polymers (1 mg/ml) were pre-diluted 1:10. (4 µl+36 µl incubation buffer); Final incubation solution was prepared by dilution 1:300 in incubation buffer (0.1% BSA in PBS) to a final concentration of 0.33 µg/ml.

100 µl of this solution were added to each well and incubated for 1 h at RT.

Thereafter, the buffer was removed and the plates were washed manually with 200 µl washing buffer per well 5 times.

Substrate Incubation

TMB-substrate was equilibrated to 25° C. for 1 h in the dark.

100 µl of substrate solution was added to each well.

The ELISA plates were incubated at 25° C. for exactly 15 min in the dark. Then the reaction was stopped by addition of 80 µl 2.5M H2SO4.

Within 5 min. after stopping the reaction, OD 450 nm was determined. After evaluation of the results, each sample returned a value for the OD.

Figure 3:
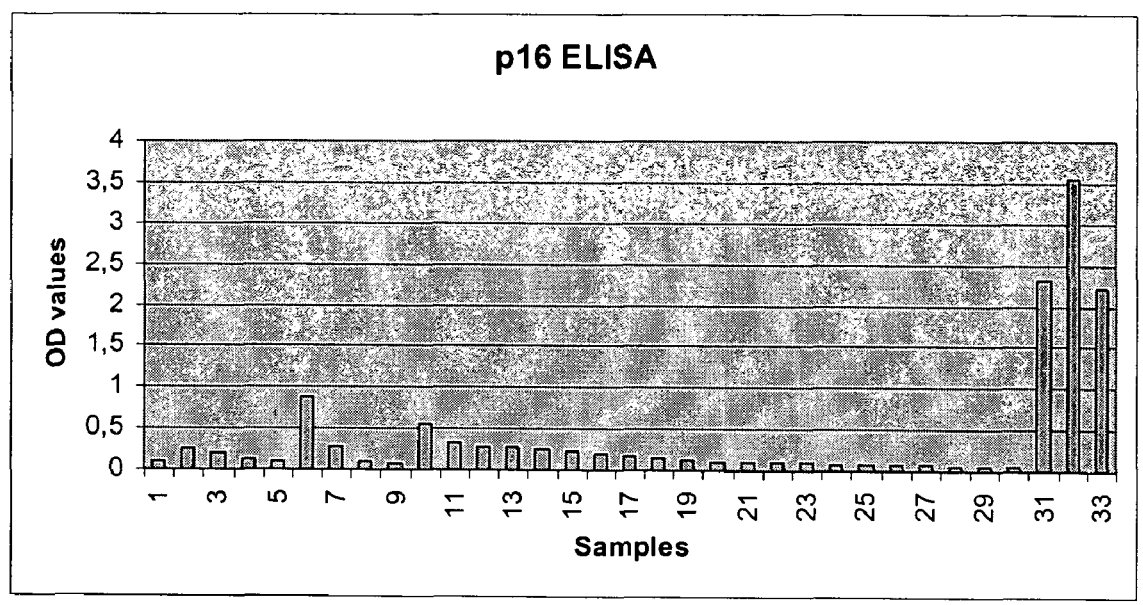
FIG. 3 shows the OD values returned in an ELISA test detecting the level of p16 in solubilized cervical samples; for experimental details see Example 3.

Results of this experiment are given in FIG. 3. The ELISA results were compared to the diagnostic results of a Papanicolaou test (PAP test, cervical cytology) from the same patients. The cervical cytology were evaluated according to the Munich Classification II (1990). Pap II encompasses benign cells, cervicitis and metaplasia, Pap IV encompasses severe dysplasia and carcinoma in situ. It turned out that samples returning an OD greater than 0.9 in the ELISA correspond to samples, that are classified as dysplastic by the conventional cytological PAP test.

Applying OD 0.9 as threshold for the evaluation of the samples, the ELISA results may be reported as follows:

TABLE 5

| Diagnosis/ELISA results | ELISA positive | ELISA negative |
| --- | --- | --- |
| Pap II | 0 | 30 |
| Pap IV | 3 | 0 |

The ELISA test is positive in all samples (100%) from women having severe dysplasia and is negative in all 30 samples (100%) of women having no dysplasia.

Using the threshold evaluated in these experiments, cytological specimens of 300 patients were tested in the presented ELISA testing format. In this experiments the specimens identified as being dysplastic by cytological examination may also be identified as dysplastic in the ELISA testing format.

The results show, that the quantification of p16 protein in solubilized patient samples allows to detect dysplasias from the samples. The diagnosis in the present example is based on the comparison of the level of p16 determined in a specific patient sample to the level known to be present in normal non-dysplastic samples. The comparison is carried out in the testing format by applying a threshold value for the OD determined in the ELISA above which the sample is to be classified as positive.

Example 4

Detection of Cervical Intraepithelial Neoplasia in an Lateral Flow Test Format

Nine cervical swabs provided in PreservCyt (Cytyc Corporation Boxborough, Mass.) solution have been subjected to conventional PAP testing and simultaneously to lateral flow based detection of overexpression of cyclin dependent kinase inhibitor p16 in solutions prepared from the cell suspensions obtained from the swabs. The lateral flow testing was performed as follows:

(A) Cell Lysis 10 ml of the cell suspensions from the individual cervical swab samples provided as PRESERVCYT® (liquid chemical pretaratory solution for use in collecting and preserving cells for examination)-fixed materials were transferred to a 15 ml reaction vessel. The samples were centrifuged 15 min at ambient temperature at 1500×g (3000 rpm, HERAEUS™ (centrifuge) Varifuge, rotor 8074); supernatant was discarded, and remaining methanol allowed to evaporate (15 min at ambient temperature); the pellet was dissolved in 500 μl mtm lysis buffer and transferred to a 1.5 ml reaction vessel. The solution was centrifuged at 4° C. (15 min at 28000×g (16600 rpm Microcentrifuge BIOFUGE® (centrifuge) fresco)); Supernatant was transferred to a fresh tube. Supernatant may be stored at −20° C.

(B) Performing the Lateral Flow Assay

Applying Capture Antibody to Membrane

Stock solution of p16 specific antibody clone mtm E6H4 was diluted in TBS (containing 1% bovine serum albumin) to give ready-to-use spotting solution with a final concentration of 1 mg antibody/ml. The ready-to-use solution was spotted onto nitrocellulose membrane at 30 μl/30 cm. Whatman wicks were attached to one end of the nitrocellulose and dipsticks are dried for 1 hour at 37° C. Then they were allowed to equilibrate at room temperature and cut into 4 mm width dipsticks.

Preparation of Conjugate Solution

Stock-solution of p16 specific antibody clone mtm D7D7, conjugated to colloidal gold (40 nm particle size) was diluted in TBS (containing 1% bovine serum albumin) to give ready-to-use detection antibody solution with a final concentration of 1.0 OD at 520 nm.

Incubation with Samples

Then 20 μl of the lysed cell samples were added to 20 μl ready-to-use detection antibody solution in a microtiter well and mixed. Dipstick, coated with capture antibody clone E6H4 was added to the well, sample was soaked and run to completion. The signal was read while the dipstick is still wet.

Results

In our testing format, 2 samples (samples 1 and 2) classified as PAP IVa by PAP staining and therefore representing dysplastic cells, gave clearly visible purple bands in the area of spotted capture antibody. In contrast, no band was detected for the other 7 samples (samples 3-9), classified as PAP II-III by PAP staining and therefore representing normal cells.

ELISA was performed by the same protocols given in Example 3. The results are shown in Table 6.

TABLE 6

| Sample | Diagnosis | ELISA OD |
| --- | --- | --- |
| 1 | Pap IVa | 2.209 |
| 2 | PAP IVa | 0.536 |
| 3 | PAP III | 0.067 |
| 4 | PAP II | 0.113 |
| 5 | PAP II | 0.095 |
| 6 | PAP II | 0.284 |
| 7 | PAP II | 0.192 |
| 8 | PAP II | 0.138 |
| 9 | PAP II | 0.07 |

The invention, and the manner and process of making and using it, are now described in such, full, clear, concise and exact terms as to enable any person skilled in the art to which it pertains, to make and use the same. It is to be understood that the foregoing describes preferred embodiments of the present invention and that modifications may be made therein without departing from the scope of the present invention as set froth in the claims. To particularly point and distinctly claim the subject matter regarded as invention, the following claims conclude this specification.

We claim:

1. A method for detecting cervical carcinomas, cervical intraepithelial neoplasms or cervical carcinomas in situ in a human subject, the method comprising the steps of:
  (a) obtaining a cervical body sample from the human subject,
  (b) solubilizing the cervical body sample in an aqueous lysis buffer comprising 0.1-1% SDS, and
  (c) reacting the solubilized cervical sample in the aqueous lysis buffer comprising 0.1-1% SDS with an antibody against cyclin dependent kinase inhibitor p16, and
  (d) determining the overexpression of cyclin dependent kinase inhibitor p16 in the solubilized cervical sample by comparing the level of cyclin dependent kinase inhibitor p16 within said solubilized cervical sample with the level present in a solubilized healthy human cervical sample, wherein cervical carcinomas, cervical intraepithelial neoplasms or cervical carcinomas in situ in the human subject are detected if overexpression of cyclin dependent kinase inhibitor p16 in the solubilized cervical sample is determined.

2. The method according to claim 1, wherein the level of cyclin dependent kinase inhibitor p16 in the healthy human cervical body sample is provided as a predetermined value to set up a threshold for the detection procedure.

3. The method according to claim 1, wherein the level of cyclin dependent kinase inhibitor p16 in a healthy human cervical sample is determined from a standardized sample solution, or from a representative number of healthy human cervical samples.

4. The method according to claim 3, wherein the determination of the level of cyclin dependent kinase inhibitor p16 in a healthy human cervical sample is carried out:
  a. in the course of the detection procedure,
  b. upon calibration of the detection system,
  c. once for each lot of detection reagents, or
  d. as a standard value for the detection method.

5. The method according to claim 1, wherein the cervical body sample is swab, smear, aspirate, biopsy, preserved cytological specimen, histological specimen, fixed cell preparation or fixed tissue preparation.

6. The method according to claim 1, wherein the cervical body sample is solubilized
   a. immediately after obtaining the sample,
   b. after storage and/or transport in a storage buffer, or
   c. after transport in a transportation buffer.

7. The method according to claim 1, wherein the lysis buffer further comprises one or more additional non-ionic or anionic detergents.

8. The method according to claim 1, wherein the lysis buffer further comprises a proteinase inhibitor.

9. The method according to claim 1, wherein the overexpression of cyclin dependent kinase inhibitor p16 in the solubilized cervical sample is determined by an ELISA.

10. The method according to claim 1, wherein the overexpression of cyclin dependent kinase inhibitor p16 in the solubilized cervical sample is determined by a lateral flow assay.

11. The method according to claim 1, wherein the overexpression of cyclin dependent kinase inhibitor p16 in the solubilized cervical sample is determined by an immunological assay selected from the group consisting of EIA, ELISA, RIA, FIA, and lateral flow assay.

12. The method according to claim 7, wherein at least one of said non-ionic detergents is t-octylphenoxypolyethoxyethanol.

13. The method according to claim 1, wherein said aqueous lysis buffer comprises 0.1% SDS.

14. The method according to claim 1, wherein said aqueous lysis buffer comprises 0.4% SDS.

* * * * *